(12) United States Patent
Poellmann

(10) Patent No.: US 6,525,549 B1
(45) Date of Patent: Feb. 25, 2003

(54) METHOD FOR DETERMINING THE CONCENTRATION OF A SUBSTANCE IN A LIQUID BY MEASURING ELECTRICAL CURRENT IN A TEST STRIP

(75) Inventor: Norbert Poellmann, Eching (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

(21) Appl. No.: 09/626,505

(22) Filed: Jul. 27, 2000

(30) Foreign Application Priority Data

Aug. 4, 1999 (DE) .......................... 199 36 693

(51) Int. Cl.[7] ............................. G01N 27/26
(52) U.S. Cl. .................. 324/717; 204/406; 205/775
(58) Field of Search ................ 324/642, 644, 324/645, 646, 717; 702/19, 108; 204/406; 205/775

(56) References Cited

U.S. PATENT DOCUMENTS 5,352,351 A * 10/1994 White et al. ................ 204/406
5,366,609 A * 11/1994 White et al. ................ 204/406
5,508,203 A * 4/1996 Fuller et al. ................ 436/149
5,589,045 A * 12/1996 Hyodo ........................ 204/406
5,985,130 A * 11/1999 Ikeda et al. ............... 205/777.5
6,051,392 A * 4/2000 Ikeda et al. ................. 435/25
6,193,873 B1 * 2/2001 Ohara et al. ................ 204/406

* cited by examiner

Primary Examiner—Ernest Karlsen
(74) Attorney, Agent, or Firm—McCormick, Paulding & Huber LLP

(57) ABSTRACT

In a method for determining the concentration of a substance in a liquid, especially for blood sugar determination, the investigated liquid is applied to the test field of a test strip (14) to be measured by way of electrical current and the resulting oxidation current in the test field is captured and evaluated. The timewise course of the oxidation current strength is captured during a calculated interval beginning with the application of the liquid, a first extreme value (34) of the current strength is compared with at least one threshold value, and an indication is produced depending on the result of the comparison.

6 Claims, 2 Drawing Sheets

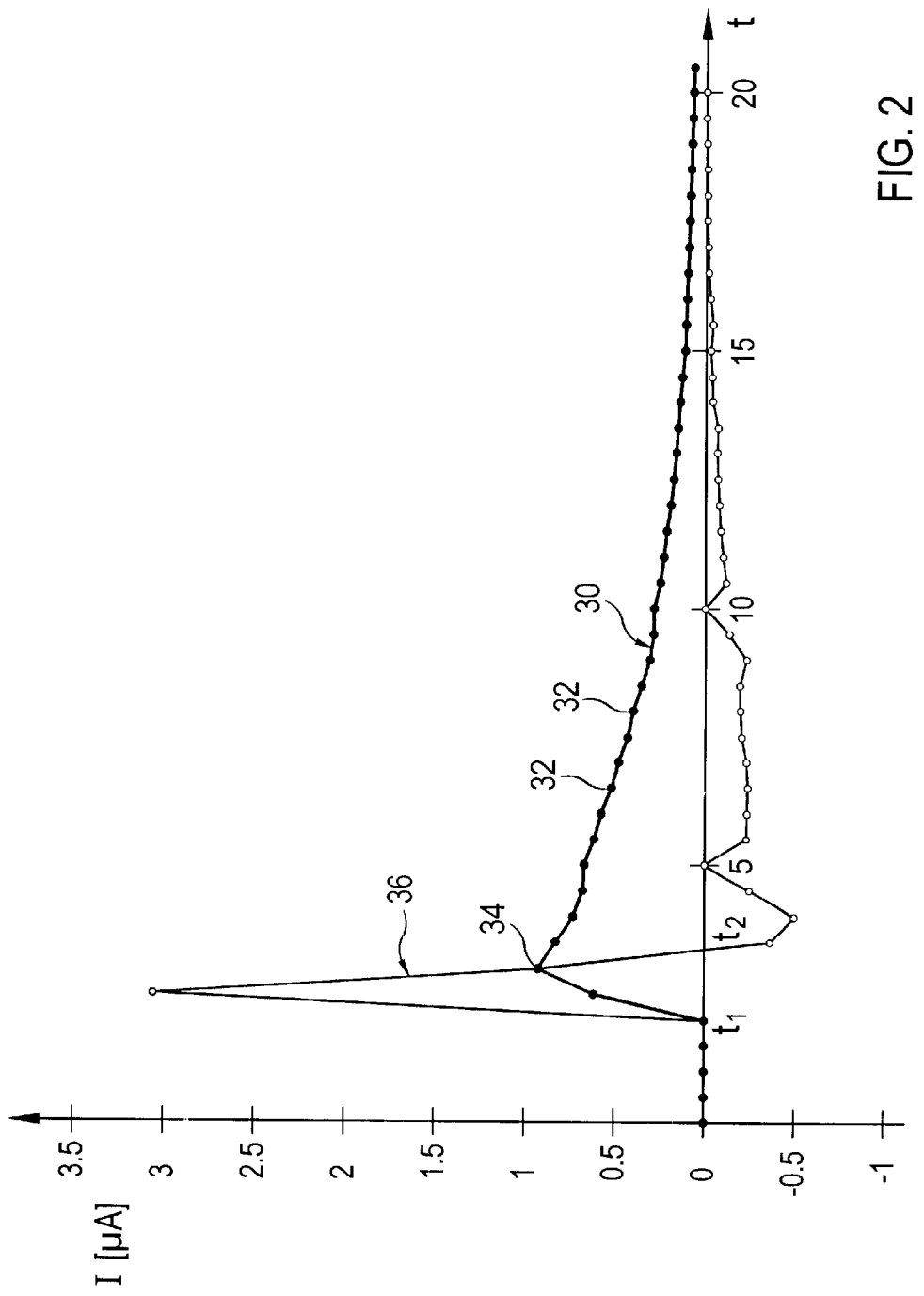

METHOD FOR DETERMINING THE CONCENTRATION OF A SUBSTANCE IN A LIQUID BY MEASURING ELECTRICAL CURRENT IN A TEST STRIP

FIELD OF THE INVENTION

The invention concerns a method for the determination of the concentration of a substance in a liquid, especially for blood sugar determination, in which the investigated fluid is applied to the test field of a test strip measured by way of electrical current, and the resulting oxidation current in the test field is captured and evaluated.

BACKGROUND OF THE INVENTION

In blood sugar measurements carried out by patients themselves, a patient applies a drop of blood onto the test field of the test strip, which is then electronically measured with a suitable electronic system capturing the strength of the oxidation current which is evoked by the application of the blood onto the test field.

In the measuring device the measured current strength is integrated over a given time and the integral value is then converted into a concentration of the looked for substance. A correct value in this case is therefore only achieved if the applied amount of blood is sufficient to uniformly wet the test field. If to the contrary the test field is only partially wetted, this leads to a falsification of the measurement, since the measured current strength on the test strip is proportional to the applied amount of blood. Therefore, such a test strip is usually specified for a minimum amount of blood, which has to be applied to the test field.

By the time this fault resulting from an insufficient dosing becomes known in the case of a customary measurement, a subsequent dosing is no longer possible because in the wetted portion of the test field the chemical reaction has already so far progressed that even with a further application of blood a correct current value is no longer achievable. Moreover, in regard to the patient, usually the small puncture wound from which the blood drop has been pressed has closed to such an extent that no further blood escapes from this site. The patient must therefore repeat the measurement which for the patient is very unpleasant if one takes into mind that a patient perhaps has to carry out the same type of measurement several times a day and each time has to stick himself in the finger.

The invention has as its object the provision of a method of the aforementioned kind in which the previously described error can be recognized in good time and in the same measuring process can yet be remedied.

SUMMARY OF THE INVENTION

This object is solved in accordance with the invention in that the timewise course of the oxidation current strength is captured during a calculated time interval beginning with the application of the liquid, that a first extreme value of the current strength is compared with at least one threshold value and in that an indication is produced in dependence on the results of the comparison. The extreme value can be a minimum or a maximum value of the current strength. This depends on the kind of the electrochemical reaction in the test field. For the determination of the current strength, the current strength is preferably sensed at the ends of sample periods, which periods are short in comparison to the sensing time interval.

The magnitude of the extreme value directly after the blood application provides a representation of whether a sufficient amount of blood has been applied. If a given extreme value is not reached, this indicates the application of too little blood. Preferably, in this case the measuring device provides an indication informing the patient or the user of the device that within a given time frame a subsequent dosing onto the same test field is possible. Therefore, by means of the inventive method, the error can be recognized and remedied before the actual test reaction and measurement for the determination of the blood sugar concentration has begun.

By a comparison of the extreme value with two threshold values, for example, a given "window" can be established within which the extreme value should lie.

According to a further feature of the invention the first derivative of the sensed timewise course of the current strength is formed and its characteristics are investigated. By means of this the exact timewise position of the extreme value which appears directly after the application of the blood is determined, so that it can be used as the zero point or beginning time point for the reaction and measuring time interval, which is involved in the determination of the looked for substance. Customary systems operate, for example, in such way, that the blood application takes place with the device turned off and that the device is first turned on after the blood application. Naturally, in such a system a reproducible starting time point for a measurement is not possible, since the time point for the start of the measuring interval always depends on the time point at which the device is turned on and therefore on the user himself. So with the method described herein a substantially better reproducibility of the measuring results is provided.

The invention further concerns a device for the determination by electrical current measurement of the concentration of a substance in a liquid, especially for blood sugar determination, including a device housing with a test strip support surface for receiving an electric current measurable test strip with a test field and with electrodes connected to the test field, a measuring and evaluation circuit connected with measuring feelers for contacting electrodes of the test strip, and an indicator device controllable by the measuring and evaluation circuit, the measuring and evaluation circuit containing a program controlled computer and structured and programmed to carry out a method of the above mentioned type.

The following description explains the invention, in combination with the accompanying drawings, by way of an exemplary embodiment.

BRIEF DESCRIPTION OF THE DRAWINGS

The drawings are:

FIG. 2—a diagram in which the current/time curve in the test field after the blood application as well as the first derivative of that curve are given.

DETAILED DESCRIPTION OF PREFERRED EMBODIMENT

Figure 1:
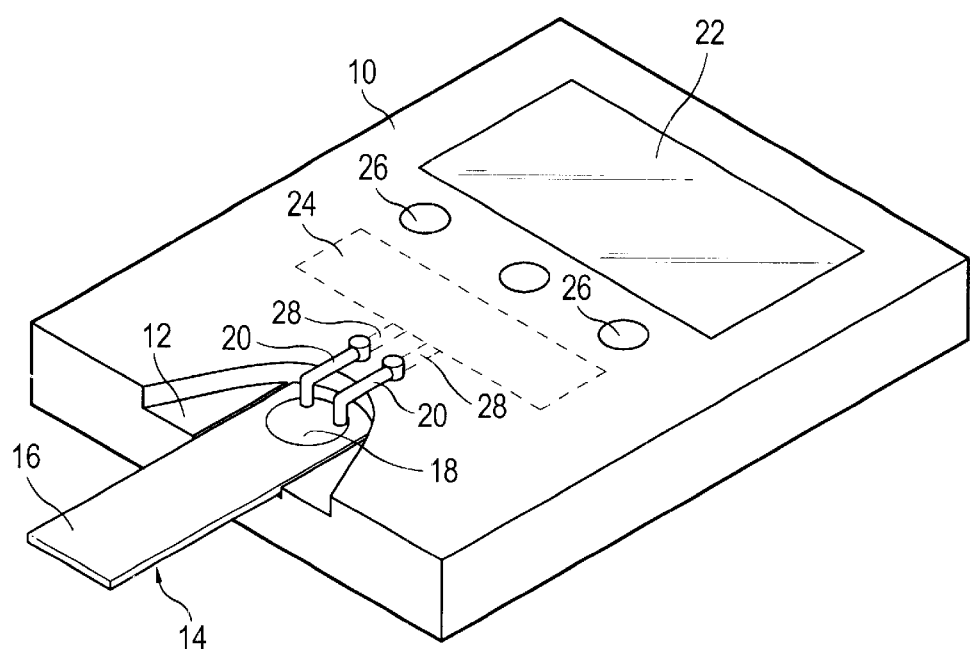
FIG. 1—a schematic illustration of a measuring device using the invention.

The measuring device illustrated in FIG. 1 includes a housing 10 with a strip support 12 onto which a test strip indicated generally at 14 is insertable. The test strip has a carrier 16 and has a portion providing a reaction zone or areal test field 18 onto which a liquid to be investigated is to be applied, with the test field 18 containing reaction chemicals which are intended to react with the looked for substance. The test field 18 is connected with two electrodes 20.

The housing 10 further contains an indicating apparatus 22, for example an LCD-indicator, a measuring and evaluation circuit 24, and operating elements 26 for manually controlling the functions of the apparatus.

The measuring and evaluation circuit contains a program-controlled computer, customarily a microprocessor, and is connected with two measuring feelers 28 designed to make contact with the electrodes 20 of the inserted test strip 14. The measuring and evaluation circuit 24 after the application of the liquid to be investigated onto the test field 18 captures the oxidation current which appears in the test field 18, evaluates this measured current with respect to the strength of the current and the timewise course of the current, and controls the indicator apparatus 22.

FIG. 2 shows a diagram in which the course of the current strength of the oxidation current appearing in the test field 18 in respect to time is given. The current strength is sensed at a sensing rate the sensing period of which is short with respect to the time interval taken into consideration. The curve 30 reproduces the typical course of the current strength with respect to time for a blood sugar determination. In it the points 32 represent the discrete sensed values.

The application of the blood onto the test field 18 occurs at the time point $t_1$. This initiates a strong change in the current strength to a maximum 34 which is reached at time point $t_2$. Thereafter, the current strength gradually declines in correspondence with the course of the reaction in the test field 18. The value of the maximum 34 depends on the amount of the applied blood. In connection with this the measuring and evaluation circuit compares the measured maximum value with a pre-given threshold value. If the threshold value is not reached, the measuring and evaluation circuit 22 informs the user through the display device 22 that the user should drop additional blood onto the test field. This information also contains the time frame within which a subsequent dosing need take place.

Simultaneously, with the determination of the timewise course of the oxidation current strength the measuring and evaluation circuit 24 also forms the first derivative of this measured curve with respect to time, as shown in FIG. 2 at 36. This allows the timewise position of the first extreme value after the blood application, that is in this case the maximum 34, and therewith the timewise beginning of the actual course of the reaction to be exactly determined. This in turn is the basis for a precise concentration determination from the measured current curve.

What is claimed is:

1. A method for the determination of the concentration of a substance in a liquid, in which the liquid to be investigated is applied to a chemical containing areal test field (18) of a test strip (14) processed by electrical current measurement and wherein an oxidation current strength effected in the test field (18) by reaction of the applied liquid with the test field chemical has a timewise course, said method comprising, providing a test strip (14) such as aforesaid, applying a quantity of a liquid to be investigated to the test field (18) of the test strip to produce a timewise course of oxidation current strength in the test field, capturing the timewise course of the oxidation current strength within a time interval calculated from the beginning of the fluid application, investigating the captured timewise course of the oxidation current strength to define a first extreme value (34) of the current strength, comparing said first extreme value (34) of the current strength with at least one threshold value, and providing an indication depending on the result of the comparison.

2. A method according to claim 1, further comprising sensing the current strength at the ends of sample periods, which periods are short in comparison to said time interval.

3. A method according to claim 1, further comprising, if in said comparing step the first extreme value (34) does not equal or exceed said threshold value, indicating a predetermined time frame within which a subsequent application of the investigated fluid onto the test field need take place.

4. A method according to claim 1, further comprising determining the time point at which the extreme value (34) of the current strength is reached and using that time point as a zero point for a timewise measurement of the reaction occurring in the test field.

5. A method according to claim 4, further comprising determining the time point at which the extreme value (34) of the oxidation current strength is reached by forming the first derivative with respect to time of the oxidation current strength/time curve.

6. A device for the electrical current determination of the concentration of a substance in a liquid, said device comprising a device housing (10) with a test strip support (12) for receiving a test strip (14) processable by way of electrical current measurement with a test field (18) and with electrodes (20) connected to the test field (18), a measurement and evaluation circuit (24) with measurement feelers (28) for contacting the electrodes (20) of the test strip (14) connected with the measurement and evaluation circuit, and an indicator device (22) responsive to the measurement and evaluation circuit (24), wherein the measurement and evaluation circuit (24) contains a computer and is structured to carry out the method according to claim 1.

* * * * *